United States Patent [19]

Howard et al.

[11] Patent Number: 5,166,382
[45] Date of Patent: Nov. 24, 1992

[54] TRANSMETALATIONS FROM ZIRCONIUM TO COPPER INTERMEDIATES

[75] Inventors: Bruce Howard Lipshutz; Edmund L. Ellsworth, both of Goleta, Calif.

[73] Assignee: Regents of the University of California, Los Angeles, Calif.

[21] Appl. No.: 747,772

[22] Filed: Aug. 20, 1991

Related U.S. Application Data

[62] Division of Ser. No. 504,370, Apr. 4, 1990, Pat. No. 5,072,010.

[51] Int. Cl.$^5$ ............................................... C07F 1/08
[52] U.S. Cl. .................................. 556/112; 556/113; 556/53; 549/356; 549/429
[58] Field of Search .................... 556/112, 113, 53; 549/356, 429

[56] References Cited

U.S. PATENT DOCUMENTS 4,777,275 10/1988 Campbell et al. ................... 356/112
4,785,124 11/1988 Campbell et al. ..................... 556/28

OTHER PUBLICATIONS

Kluge et al., J. Amer. Chem. Soc., vol. 94, No. 22, pp. 7827–7832 (1972).

Primary Examiner—Jose G. Dees
Assistant Examiner—Porfirio Nazario
Attorney, Agent, or Firm—Robbins, Dalgarn, Berliner & Carson

[57] ABSTRACT

Higher order cuprate complexes are prepared by means of a transmetalation from a corresponding zirconate intermediate. This process is particularly valuable with respect to the preparation of vinylic side chains such as are present in prostaglandins, as it is possible in accordance with the present invention to proceed directly from the acetylenic precursors via the reactive cuprates to the desired final products in a one-pot operation without isolation of intermediates and in high yields. Sequential additions to zirconium intermediates of components which together comprise the cuprate involved in transmetalation with the zirconium intermediate are disclosed as alternative procedures.

10 Claims, No Drawings

TRANSMETALATIONS FROM ZIRCONIUM TO COPPER INTERMEDIATES

This is a divisional of U.S. Pat. application Ser. No. 07/504,370 filed Apr. 4, 1990, now U.S. Pat. No. 5,072,010.

BACKGROUND OF THE INVENTION

This invention relates to the field of organometallic chemistry. In particular, this invention relates to methods for the preparation of organometallic complexes useful as reactive intermediates in organic synthesis, especially for the formation of carbon-to-carbon bonds.

The utility of organocopper complexes as reactive intermediates in a variety of synthetic reactions has been well known for decades. Particularly important reactions utilizing organocopper complexes in the formation of carbon-to-carbon bonds include addition reactions (such as 1,4-conjugate additions and carbocupration reactions) and substitution reactions (such as, for example, the displacement of halides, tosylates or mesylates and ring opening of epoxides). In such reactions, the organocopper complex formally serves as the source of a suitable carbanion for introduction into a target molecule by addition or displacement.

Early work in the field of organocopper chemistry involved treatment of either catalytic or stoichiometric quantities of a copper(I) halide with a Grignard (RMgX) or organolithium (RLi) reagent. The resultant products are either neutral organocopper reagents RCu(I) or copper(I) monoanionic salts $R_2CuM$ (M =Li or MgX), commonly referred to as lower order or Gilman reagents. Copper(I) cyanide is also an excellent precursor for the direct formation of lower order cyanocuprates RCu(CN)Li upon treatment with an equivalent of an organolithium. It is believed that the strength of the Cu-CN linkage accounts for the direct cuprate formation with one equivalent of the organolithium, rather than the metathesis that occurs with copper(I) halides to produce an equivalent of LiX.

While such lower order complexes have some direct synthetic applications, it has further been determined that reagents of this type can be composed of different ligands (i.e., R≠R'). In other words, rather than forming a complex of the formula $R_2CuLi$ from two equivalents of the same RLi, different organolithium compounds can be used to provide a complex of the formula $R_TR_RCuLi$. In this manner, it is possible to conserve potentially valuable $R_TLi$. Successful exploitation of such complexes comprising two different ligands is based on the ability to control the selectivity of transfer of the desired ligand $R_T$ rather than the residual (or "dummy") group $R_R$ from copper to electrophilic carbon.

A particularly significant advance in the field of organocopper complexes has been the development of so-called "higher order" cuprates For example, the admixture of two equivalents of RLi (or one equivalent each of $R_TLi$ and $R_RLi$) with copper(I) cyanide proceeds to the formation of a copper(I) dianionic complex or higher order cyanocuprate, $R_2Cu(CN)Li_2$ The cyano ligand, with its π-acidic nature, is believed to enable the copper to accept a third negatively-charged ligand in ethereal solvents (e.g., $Et_2O$ and THF). Such higher order complexes, particularly those derived from two different organolithium compounds, have been successfully exploited as highly selective and efficient means of making key carbon-to-carbon bonds.

The use of cuprates in 1,4-conjugate addition reactions for introduction of unsaturated carbanions is especially attractive due to the complete control of double bond geometry in the reaction scheme. This is of particular significance, for example, in the synthesis of various prostaglandins via conjugate addition of an alkenyl moiety to the unsaturated ketone functionality of a substituted cyclopentenone.

To date, the preparation of reactive vinylic organocuprate reagents has involved a limited number of typical reaction pathways In particular, for transfer of a particular alkenyl side chain to a target molecule, either a vinylic halide (usually, the bromide or iodide) or a vinylic stannane has usually been employed as a precursor molecule. These precursor molecules are generally prepared from a corresponding acetylene and converted to the reactive copper reagents for use as synthetic intermediates.

U.S. Pat. No. 4,777,275 to Campbell et al., the disclosure of which is hereby incorporated by reference, describes a process for preparing a higher order copper complex in which a ligand (designated $R_t$) which is desired in a subsequent synthetic organic reaction to form a new carbon-to-carbon bond is transferred in situ from a stannane compound to a first higher order copper complex to form a second higher order copper complex including the ligand. Of course, to employ this method it is first necessary to prepare specific vinyl stannanes by art recognized techniques. Such techniques generally call for the reaction of a suitable acetylene with, e.g., a trialkyl tin hydride. Unfortunately, the stannanes are generally quite toxic. Therefore, it would be advantageous to avoid such intermediates entirely if possible.

Preparation of suitable cuprate complexes from the corresponding halides is also problematic, particularly in the case of alkenylhalides. Formation of the desired cuprates is generally effected from the corresponding alkenyllithium compounds, which in turn are prepared by metal-halogen exchange (typically using two equivalents of highly pyrophoric and expensive t-butyllithium) with the corresponding alkenylhalides or reaction of the halides with lithium metal. Preparation of the organolithium precursors via this latter method is typically tedious, and may result in low yields. Moreover, in the case of the alkenyl compounds, there may be some loss of double-bond stereochemistry.

According to U.S. Pat. No. 4,415,501 to Grudzinskas et al., the disclosure of which is also hereby incorporated by reference, some of the potentially problematic issues associated with the chemistry involved in the formation of vinylic cuprate complexes are avoided by utilizing an alternative class of reagents. A class of alkenylzirconium reagents are described, which may be employed directly in various conjugate addition reactions. These alkenylzirconium reagents are prepared by reaction of the corresponding protected alkynol with dicyclopentadienyl zirconium chlorohydride; the latter is typically generated in situ by the reduction of dicyclopentadienyl zirconium dichloride in solution under an inert atmosphere. The thus-prepared alkenylzirconium reagents are described as moisture sensitive, and thus it is suggested that they are best prepared just prior to use. Reaction of the alkenylzirconium reagents with the target molecule for a conjugate addition is effected in the presence of a catalytic amount of a reduced nickel catalyst.

While the method of U.S. Pat. No. 4,415,501 obviates some of the potential problems associated with the formation of the reactive cuprates, it does so at the cost of yield and purity of the resultant products, as is immediately apparent from a review of Table II of the reference. Indeed, while the products of hydrozirconation reactions may be utilized in selected coupling reactions to form carbon-to-carbon bonds, there is no general established method for directly transferring these ligands to alpha, beta unsaturated ketones in a conjugate (i.e., 1,4-) sense. Therefore, the reference method using organozirconium compounds directly as reagents is limited in applicability and clearly unacceptable for the preparation of most products, in particular from relatively expensive optically-active intermediates, on a commercial scale.

It is an object of the present invention to provide a method for the preparation of suitable organometallic intermediates for use in the transfer of a particular carbanion equivalent (e.g., a vinylic organometallic species) to a target molecule with the formation of carbon-to-carbon bonds pursuant to the heretofore known reaction mechanisms involving such carbanions.

In particular, it is an object of the present invention to provide a method for the preparation of reactive organometallic intermediates which results in a high yield of both the intermediates and of the final products prepared via such intermediates.

In addition, it is a further object of the present invention to provide a method for the preparation of reactive organometallic intermediates for use in the preparation of a variety of products exploiting known reaction mechanisms formally involving carbanions (such as 1,4-conjugate additions or displacement reactions) without the need to prepare or isolate halide or stannane precursors of the subject organometallics.

SUMMARY OF THE INVENTION

In accordance with the present invention, higher order cuprate complexes of the type described in, e.g., U.S. Pat. No. 4,785,124 to Campbell et al., are prepared by means of a transmetalation from a corresponding zirconate intermediate. This process is particularly valuable with respect to the preparation of vinylic side chains such as are present in prostaglandins, as it is possible in accordance with the present invention to proceed directly from the acetylenic precursors via the reactive cuprates to the desired final products in a one-pot operation without isolation of intermediates and in high yields. Thus, the problems associated with the preparation of the corresponding vinyl halides or stannanes are avoided entirely.

DETAILED DESCRIPTION OF THE INVENTION

In accordance with the present invention, there is provided a novel method for the preparation of a cuprate complex of the general formula I

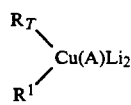

wherein $R_T$ is a ligand (as hereinafter defined) which will participate in carbon-to-carbon bond formation; $R^1$ is different from $R_T$ and is selected from the group consisting of alkyl, alkenyl, alkynyl, allylic, aryl, benzylic and heterocyclic moieties, $-BR^3$ wherein B is O or S and $R^3$ is an alkyl, alkenyl, alkynyl, allylic, aryl, benzylic or heterocyclic moiety, and $-NR^4R^5$ wherein $R^4$ and $R^5$ are the same or different and each is an alkyl, alkenyl, alkynyl, allylic, aryl, benzylic or heterocyclic moiety, said moieties being unsubstituted or substituted by non-interfering substituents; and A is CN or SCN.

In accordance with the method of the present invention, a zirconium intermediate of general formula II

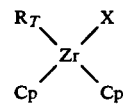

wherein Cp represents a cyclopentadienyl moiety which is unsubstituted or substituted by non-interfering substituents (e.g., pentamethylcyclopentadienyl), X is halogen (e.g., Cl, Br, I) and $R_1$ is as previously defined, is treated by addition of a compound of general formula $R^2M$ (e.g., $R^2Li$ or $R^2MgX$), wherein M is a suitable metal, X is halogen and $R^2$ is defined in the same manner as $R^1$ and may be the same as or different from $R^1$, to prepare an intermediate of general formula III

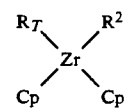

wherein $R_T$ and $R_2$ are as previously defined.

Without isolation, the intermediate of general formula III is reacted in accordance with a preferred embodiment of the inventive method with a stable, storable cuprate reagent of formula $R^1{}_2Cu(A)Li_2$, wherein $R^1$ and A are as previously defined, to provide the compound of general formula I via transmetalation from the zirconium intermediate in very high yield.

As an alternative to the above procedure (designated as reaction path A in Scheme 1), pursuant to one alternative the higher order cuprate I may be realized by sequential additions of the elements of $R^1{}_2Cu(A)Li_2$. For purposes of clarity, the following discussion will refer to R', defined in the same manner as $R^1$. As $R'{}_2Cu(A)Li_2$ is composed of 2 R'Li plus Cu(A), cuprate I can be prepared via addition of two equivalents of R'Li to intermediate II, followed by introduction of one equivalent of R'Cu(A)Li, as illustrated in reaction path B in Scheme 1. Yet another variant procedure calls for addition of three equivalents of R'Li to zirconate II, followed by one equivalent of Cu(A), the latter as a solid or in a LiX-solubilized form [e.g., Cu(A).nLiX, wherein n is an integer from 1 to 10] in solution in an ethereal solvent as per reaction path C in Scheme 1. As all of these alternatives proceed from the zirconate II, and as the overall reaction pursuant to each alternative is believed to involve at least some transmetalation from zirconium to copper, these alternatives are all viewed as aspects of the present invention.

Moreover, it is clearly not essential that, ultimately, three equivalents of the same R'Li be used; various combinations of organolithium reagents are acceptable. This is illustrated in Scheme 2, wherein the use of up to three different reagents is contemplated. Each of R', R'' and R''' is a group falling within the definition previously given for $R^1$; while any two or all three of R', R" and R'" may be the same, all three may be different. As according to Scheme 2 a variety of zirconates and cuprates may be formed, the various products are designated using groups $R^A$, $R^B$ and $R^C$, each of which corresponds to one of R', R" and R'" in the starting materials. In the final product of general formula I, $R^1$ thus corresponds to one of R', R" and R'".

sentative procedures are described infra (see Example 4, relating to Scheme 1, path B and Example 5, relating to Scheme 1, path C) which establish unequivocally that the order of mixing is irrelevant to the net transmetalation scheme leading to cuprate I.

SCHEME 1

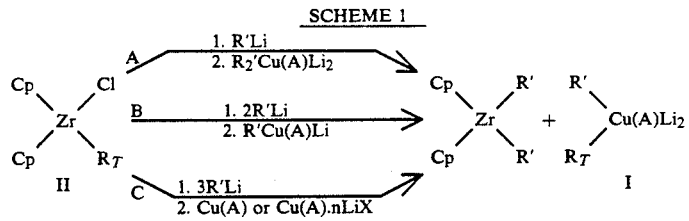

SCHEME 2

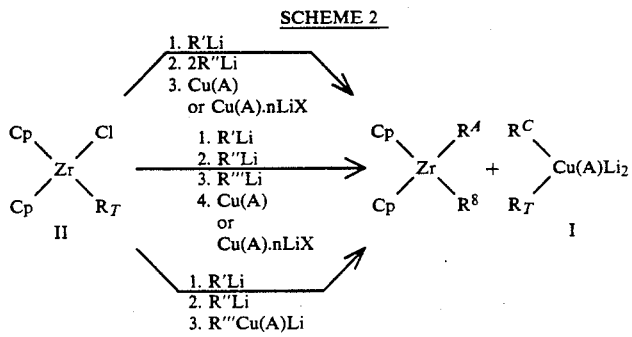

In terms of mechanism, it is not presently known precisely how zirconate III and a higher order cuprate exchange ligands to provide the product of general formula I. Initially, it is believed that addition of a first equivalent of R'Li to intermediate II produces zirconate III via a simple transmetalation from lithium to zirconium. Under the influence of excess R'Li, however, other events may well take place, leading to a mix of discrete organolithium reagents prior to introduction of any source of Cu(I), such as R'Cu(A)Li, Cu(A) or Cu-(A).nLiX. Depending on the nature of R'Li, addition of >1 equivalent of R'Li to zirconate II may well establish an equilibrium including free $R_TLi$, as shown below:

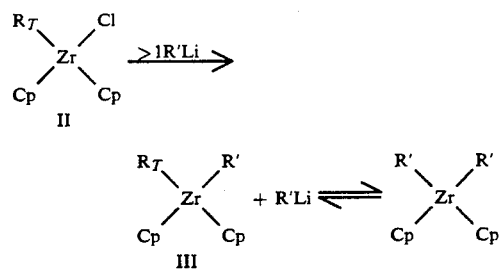

Although not yet proven, it has been suggested that such a phenomenon may occur [Negishi, E. et al., Aldrichimica Acta 18, 31 (1985)]. The extent of the equilibrium giving rise to $R_TLi$, if it exists at all, is not predictable. Irrespective of such a potential equilibrium, the thermodynamic sink for the overall process ultimately places the $R_T$ ligand on copper, whether via direct ligand exchange between intermediate III and a higher order cuprate, or by cuprate formation using equilibria-generated $R_TLi$ and an alternate Cu(I) source. Repre- The resultant solution containing the compound of general formula I may be used directly in subsequent reactions (such as, e.g., conjugate additions or displacement reactions) to -transfer the ligand $R_T$ to the target molecule in very high yields. The product may then be recovered using known methods. All reactions are preferably carried out under an inert atmosphere (e.g., argon).

In accordance with a preferred embodiment of the inventive method, the zirconium intermediate of general formula II is prepared in a manner known per se by a hydrozirconation reaction which comprises reacting a suitable ligand precursor compound (as hereinafter defined) for the carbanion $R_T$ with a compound of the formula $Cp_2Zr(H)Cl$, wherein Cp is as previously defined. Typically, Cp represents an unsubstituted cyclopentadienyl moiety, in which case the compound of the formula $Cp_2Zr(H)Cl$ corresponds to the well-known Schwartz reagent for hydrozirconation. Alternatively, the zirconium intermediate may be prepared by other methods known per se.

In the above formulas, $R_T$ represents an anionic ligand corresponding to a chain or cyclic array which it is desired to introduce into a final product. As is well recognized in the art, an extremely wide variety of ligands for use in reactions such as 1,4-conjugate additions and displacements may be introduced into the known higher order reactive cuprate complexes of general formula I. In particular, the ligands $R_T$ in accordance with the present invention comprise a broad range of structures that may be transferred in situ from a zirconate complex to replace an alkyl ligand in a cuprate complex in accordance with the method of the present invention. Exemplary classes of anionic ligands are, for example, those discussed in the aforementioned U.S. Pat. No. 4,777,275. Ligands $R_T$ of interest include:

alkyl, such as straight or branched-chain alkyl and typically comprising one to about 20 carbon atoms, or cycloalkyl of three to about 20 carbon atoms; alkenyl, such as terminal and/or internal olefins and typically comprising two to about 20 carbon atoms, or cycloalkenyl of three to about 20 carbon atoms; aryl, such as phenyl, naphthyl and phenanthryl; allylic; and benzylic moieties.

Of particular interest for purposes of organic synthesis are those ligands $R_T$ which contain at least one unsaturation in the ligand carbon chain. The electronic configuration of such ligands apparently makes them particularly susceptible to the desired transmetalation from zirconium to copper. Ligands $R_T$ selected from the group consisting of terminal alkenyl, aryl, allylic and benzylic ligands are preferred for use in accordance with the present invention.

The inventive method is of special utility in connection with ligands $R_T$ comprising the beta side chain of a natural or synthetic prostaglandin. In such side chains, any hydroxy groups present are generally protected from undesired side-reactions in a manner heretofore known per se (for example, by trialkylsilyl, tetrahydropyranyl or tetrahydrofuranyl moieties).

In accordance with the present invention, all of the aforesaid classes of ligands $R_T$ include both the unsubstituted moieties and those which are substituted by one or more non-interfering substituents. By non-interfering substituents is meant substituents which do not engage in undesirable side-reactions or rearrangements in the copper or zirconium complexes, and which do not hinder reaction due to steric and/or electronic factors. For example, suitable non-interfering substituents include alkyl, phenyl, alkoxy, phenoxy, halogen, and protected hydroxy (i.e., a hydroxyl group which is protected by one of a variety of protective groups which are known per se) and the like. In addition, carbanions containing aldehyde, ketone and carboxyl functional groups which are suitably protected in a manner known per se may successfully be employed in accordance with the inventive method [see Schwartz et al., supra. at 339]. Typically, the substituents comprise lower alkyl qroups or derivatives thereof, wherein lower alkyl represents straiqht- or branched-chain alkyl of one to six carbons or cycloalkyl of three to six carbon atoms. As the transmetalation may be effected at reduced temperatures (for example, on the order of about $-78°$ C.) and occurs rapidly, the inventive method provides the particular advantage that various functionalities which might otherwise be susceptible to undesired side-reactions during the reaction sequences heretofore employed for preparation of reactive cuprate complexes (for example, by a method as described in the aforementioned U.S. Pat. No. 4,777,275) may be included in carbanions as prepared by a transmetalation process in accordance with the present invention. Similarly, the presence of non-interfering substituents on other reactants employed in accordance with the inventive method has no adverse impact on the reaction mechanisms contemplated herein.

As previously noted, the zirconium intermediate of general formula II may be prepared in a manner known per se, for example from a suitable ligand precursor compound (e.g., an acetylene). In accordance with a preferred embodiment of the present invention, the provision of ligand $R_T$ may suitably be carried out by selection of a ligand precursor compound which provides the desired ligand via a hydrozirconation reaction with a compound of formula $Cp_2Zr(H)X$ in a manner known per se [see, e.g., Schwartz, J. et al., Angew. Chem. Int. Ed. Engl. 15(6). 333 (1976)]. For example, reaction of a 1-alkynyl compound results in the formation of an intermediate comprising the corresponding 1-alkenyl ligand (i.e., a vinylzirconate) similarly, reaction of a 1-alkenyl precursor provides an intermediate comprising the corresponding alkyl ligand (i.e., an alkylzirconate). The use of non-terminal alkynyl or alkenyl carbanion precursor compounds generally results in the formation of zirconates by placement of the zirconium moiety at the sterically least hindered position of the precursor chain as a whole, for example by Zr-H addition to an internal multiple bond followed by rapid rearrangement via Zr-H elimination and readdition to place the metal in each case at the less hindered position of the alkyl chain. Hydrozirconation of 1,3-dienes proceeds by 1,2-addition to the sterically less hindered double bond to give gamma, delta-unsaturated alkylzirconium complexes in high yield; similarly, hydrozirconation of conjugated enzymes to produce dienylzirconium derivatives has also been shown to proceed as predicted. In general, the products of such reactions are determined by size exclusion phenomena based primarily on steric effects. In some instances, the alternative procedures discussed supra and/or other known procedures for preparation of the zirconium complexes of general formula II (such as transmetalation or oxidative addition) may also suitably be employed to provide a particular anionic ligand $R_T$ (see. e.g., Negishi, E. et al., Synthesis, 1988, 1).

In a particularly preferred embodiment of the present invention, the zirconium intermediate of general formula II is prepared by reaction of a compound of the formula $Cp_2Zr(H)Cl$ with a 1-alkynyl compound of general formula R-C H, wherein R is selected from the group consisting of alkyl, alkenyl, aryl, allylic and benzylic moieties, said moiety being unsubstituted or substituted by non-interfering substituents. In this manner, it is possible to prepare higher order cuprates comprising valuable vinylic ligands (for example, those corresponding to the beta side chains characteristic of prostaglandin analogs) directly from the corresponding 1-alkynes. A particular advantage of this preferred embodiment of the invention is that it is unnecessary to isolate the zirconium intermediate of general formula II from the reaction mixture in which it is formed. Thus, in accordance with this preferred embodiment of the inventive method, it is possible to introduce a vinylic side chain into a target enone in a one-pot reaction proceeding from the corresponding 1-alkyne.

After formation of the intermediate zirconate of general formula II, in accordance with a particularly preferred procedure (reaction path A in Scheme 1) addition to the reaction solution of one equivalent of $R^2Li$ is generally carried out at low temperatures (e.g., about $-78°$ C.) to form the intermediate of general formula III. After cooling (for example to $-78°$ C.), a cooled solution of $R^1{}_2Cu(A)Li_2$ (prepared, for example, by the reaction of two equivalents of $R^1Li$ with CuCN in a suitable solvent at $-78°$ C.). is added and the solution allowed to stir at this temperature for a relatively short period of time (e.g., approximately 15 minutes). Following the transmetalation to form the mixed higher order cuprate of general formula I, the reagent may be employed directly without isolation from the reaction medium. The alternative procedures described supra are also preferably carried out at reduced temperatures (i.e., generally below room temperature). Suitable solvents include tetrahydrofuran (THF), substituted tetrahydrofuran, dimethyl ether diethyl ether, dimethoxyethane (DME), dimethyl sulfide (DMS), methylene chloride, toluene, benzene, dibutyl ether, t-butyl methyl ether, boron trifluoride and mixtures thereof.

Pursuant to a further preferred embodiment of the inventive method, the cuprate complex of general formula I is used as a source of an anionic ligand $R_T$ without isolation thereof from the reaction medium. For example, a target reactant for said anionic ligand may be added directly to the reaction medium, so as to achieve a desired 1,4-conjugate addition reaction, substitution reaction, etc. The cuprate complex of general formula I may suitably be used in the presence of one or more additives. Exemplary additives include Lewis acids, such as boron trifluoride etherate ($BF_3.Et_2O$); silyl halides, such as trimethylsilyl chloride ($Me_3SiCl$); phosphines, such as tri-n-butylphosphine (n-$Bu_3P$); amines, such as tetramethylethylenediamine, TMEDA ($Me_2NCH_2CH_2NMe_2$); and various alkali metal salts, including halides and alkoxides (e.g., lithium halides or alkoxides, LiX/LiOR).

As illustrated by the results reported in Table I, the method of the present invention permits the direct formation of mixed higher order cuprates which selectively deliver a desired ligand to a target molecule without isolation of the reactive cuprates or intermediates in the preparation thereof. Of particular interest is the introduction of beta side chains characteristic of prostaglandin analogs, such as that found in the potent antisecretory agent misoprostol, without recourse to vinylic halide or stannane intermediates.

The invention will be better understood by reference to the following examples which are intended for purposes of illustration and are not to be construed as in any way limiting the scope of the present invention, which is defined in the claims appended hereto.

EXAMPLE 1

Preparation of
3-(1-t-Butyldiohenylsiloxy-2-propen-3-yl)-4-isopropyl-cyclohexanone A 10 mL round-bottom flask equipped with a stir bar was charged with zirconocene chloride hydride (0.129 g, 0.50 mmol) and sealed with a septum. The flask was evacuated with a vacuum pump and purged with argon, the process being repeated 3 times. THF (0.75 mL) was injected and the mixture stirred to generate a white slurry which was treated via canula with 1-t- butyldiphenylsiloxy-2-propyne (0.147 g, 0.50 mmol) as a solution in THF (0.75 mL). The mixture was stirred for 15 minutes to yield a nearly colorless solution which was cooled to $-78°$ C. and treated via syringe with ethereal MeLi (0.33 mL, 0.50 mmol) to generate a bright yellow solution. Depending upon the quality of the MeLi, the yield of isolated product may vary. Impurities (especially lithium alkoxides) may have a detrimental impact. MeLi, available commercially in cumene-THF, may also be used in place of ethereal MeLi. Concurrently, CuCN (0.045 g, 0.50 mmol) was placed in a 5 mL round-bottom flask equipped with a stir bar, and sealed under septum. The flask was evacuated and purged with argon as above and DME (1.0 mL) added via syringe. The resulting slurry was cboled to $-78°$ C. and treated with MeLi in ether (0.66 mL, 1.0 mmol). The mixture was warmed to yield a suspension of $Me_2Cu(CN)Li_2$ which was recooled to $-78°$ C. and added via canula to the zirconium solution. The mixture was stirred for 15 minutes at $-78°$ C. to yield a bright yellow solution which was treated with 4-isopropyl-2-cyclohexenone (0.037 mL, 0 25 mmol). After 10 minutes the mixture was quenched with 10 mL of 10% $NH_4OH$ in saturated $NH_4Cl$. The product was extracted with $3\times30$ mL of ether and dried over $Na_2SO_4$. The solution was then filtered through a pad of celite and the solvent removed in vacuo. The resulting residue was submitted to flash chromatography on silica gel (Petroleum Ether/Ethyl Acetate, 9/1) to give a quantitative yield (0.108 g) of 3-(1-t-butyldiphenyl-siloxy-2-propen-3-yl)-4isopropyl-cyclohexanone (product 1 in Table I) as a colorless oil which gave satisfactory IR, NMR, MS, and HRMS data.

EXAMPLE 2

Preparation of 3-(1-octen-1-yl)-cyclohexenone

A 10 mL round-bottom flask equipped with a stir bar was charged with zirconocene chloride hydride (0.129 g, 0.50 mmol) and sealed with a septum. The flask was evacuated with a vacuum pump and purged with argon, the process being repeated 3 times. THF (1.5 mL) was injected and the mixture stirred to generate a white slurry which was treated via canula with 1-octyne (0.147 g, 0.50 mmol). The mixture was stirred for 15 minutes to yield a nearly colorless solution which was cooled to $-78°$ C. and treated via syringe with ethereal MeLi (0.35 mL, 0.50 mmol) to generate a bright yellow solution. Concurrently, CuCN (0.045 g, 0.50 mmol) was placed in a 5 mL round-bottom flask equipped with a stir bar, and sealed under septum. The flask was evacuated and purged with argon as above and THF (1.0 mL) added via syringe. The resulting slurry was cooled to $-78°$ C. and treated with MeLi in ether (0.70 mL, 1.0 mmol). The mixture was warmed to yield a colorless solution of $Me_2Cu(CN)Li_2$ which was recooled to $-78°$ C. and added via canula to the zirconium solution. The mixture was stirred for 15 minutes at $-78°$ C. to yield a yellow solution which was treated with 2-cyclohexenone (0.024 mL, 0.25 mmol). After 5 minutes the mixture was quenched with 5 mL of 10% $NH_4OH$ in saturated $NH_4Cl$. The product was extracted with $3\times20$ mL of ether and dried over $Na_2SO_4$. The solution was then filtered through a pad of celite and the solvent removed in vacuo. The resulting residue was submitted to flash chromatography on silica gel (Petroleum Ether-/Ethyl Acetate, 9/1) to give an 86% yield (0.108 g) of 3-(1- octen-1-yl)-cyclohexanone (product 2 in Table 1) as a colorless oil which gave satisfactory IR, NMR, MS, and HRMS data.

Using procedures analogous to those described in Examples 1 and 2, the products 3-6of Table I are prepared from the corresponding educts and acetylenes and under the conditions indicated therein.

EXAMPLE 3

Preparation of misoprostol

A 10 mL round-bottom flask equipped with a stir bar was charged with zirconocene chloride hydride (0.129 g, 0.50 mmol) and sealed with a septum. The flask was evacuated with a vacuum pump and purged with argon, the process being repeated 3 times. THF (1.50 mL) was injected and the mixture stirred to generate a white slurry which was treated with trimethyl-[(1-methyl-1-(2- propynl)-pentyl)-oxy]silane (0.124 mL, 0.50 mmol).

The mixture was stirred for 15 minutes to yield a nearly colorless solution which was cooled to −78° C. and treated via syringe with ethereal MeLi (0.35 mL, 0.50 mmol) to generate a bright yellow solution. Concurrently, CuCN (0.045 g, 0.50 mmol) was placed in a 5 mL round-bottom flask equipped with a stir bar, and sealed under septum. The flask was evacuated and purged with argon as above and ether (0.50 mL) added via syringe. The resulting slurry was cooled to −78° C. and treated with MeLi in ether (0.70 mL, 1 0 mmol). The mixture was warmed to yield a suspension of Me$_2$Cu(CN)Li$_2$ which was recooled to −78° C. and added via canula to the zirconium solution. The mixture was stirred for 15 minutes at −78° C. to yield a bright yellow solution which was treated via canula with methyl 7-(5-oxo-3-[(triethylsilyl)-oxy]-1-cyclopenten-1-yl)-heptanoate (0.088 mL, 0.25 mmol) in ether (0.50 mL). After 10 minutes the mixture was quenched with 20 mL of 10% NH$_4$OH in saturated NH$_4$Cl. The product was extracted with 3×30 mL of ether and dried over Na$_2$SO$_4$. The solution was then filtered through a pad of celite and the solvent removed in vacuo. The resulting residue was submitted to flash chromatography on silica gel (Petroleum Ether/Ethyl Acetate, 9/1) to yield 0.132 g of the protected form of misoprostol (product 7 in Table I) in a 92% yield as a colorless oil which was compared with authentic material.

EXAMPLE 4

Preparation of 3-(1-Phenvlethen-2-vl)-3,5,5-trimethvlcyclohexanone

A 10 mL round-bottom flask equipped with a stir bar was charged with zirconocene chloride hydride (0.258 g, 1.0 mmol) and sealed with a septum. The flask was evacuated with a vacuum pump and purged with argon, the process being repeated 3 times. THF (3.0 mL) was injected and the mixture stirred to generate a white slurry which was treated via syringe with phenyl acetylene (0.110 mL, 1.0 mmol). The mixture was stirred for 15 minutes to yield a bright red solution which was cooled to −78° C. and treated via syringe with ethereal MeLi (1.40 mL, 2.0 mmol). Concurrently, CuCN (0.0895 g, 1.0 mmol) was placed in a 5 mL round-bottom flask equipped with a stir bar, and sealed under septum. The flask was evacuated and purged with argon as above and THF (1.0 mL) added via syringe. The resulting slurry was cooled to −78° C. and treated via canula with a solution of 2-thienyllithium prepared from the metalation of thiophene (0.080 mL, 1.0 mmol) with n-BuLi (0.43 mL, 1.0 mmol) in THF (1.50 mL). The mixture was warmed to yield a suspension of (2-thienyl)Cu(CN)Li which was recooled to −78° C. and added via canula to the zirconium solution. The mixture was stirred for 30 minutes at −78° C. to yield a bright red solution which. was treated with BF$_3$.Et$_2$O (0.12mL, 1.0 mmol) followed by the addition of isophorone (0.075 mL, 0.5 mmol). After 1 hour the mixture was quenched with 10 mL of 10% NH$_4$OH in saturated NH$_4$Cl. The product was extracted with 3×50 mL of ether and dried over Na$_2$SO$_4$. The solution was then filtered through a pad of celite and the solvent removed in vacuo. The resulting residue was submitted to flash chromatography on silica gel (Petroleum Ether/Ethyl Acetate, 9/1) to give a 71% yield (0.086 g) of 3-(1phenylethen-2-yl)-3,5,5-trimethylcyclohexanone (product 3 in Table I) as a thick yellow oil which gave satisfactory IR, NMR, MS and HRMS data. The above procedure can alternatively be carried out with commercially-available (2-thienyl)Cu(CN)Li (2.94 mL, 1.0 mmol) which when cooled to −78° C. can be added directly to the zirconium mixture.

EXAMPLE 5

Preparation of 3-(1-octen-1-vl)-cyclohexenone

A 10 mL round-bottom flask equipped with a stir bar was charged with zirconocene chloride hydride (0.258 g, 1.0 mmol) and sealed with a septum. The flask was evacuated with a vacuum pump and purged with argon, the process being repeated 3 times. THF (2.0 mL) was injected and the mixture stirred to generate a white slurry which was treated with 1-octyne (0.148 mL, 1.0 mmol) as a solution in THF (0.75 mL). The mixture was stirred for 15 minutes to yield a yellow-orange solution which was cooled to −78° C. and treated via canula with a THF (2.0 mL) solution of MeLi (2.71 mL, 3.0 mmol)/cumene to generate a bright yellow solution. Concurrently, CuCN (0.0895 g, 1.0 mmol) and LiCl (0.085 g, 2.0 mmol) were placed in a 5 mL round-bottom flask equipped with a stir bar, and sealed under septum. The flask was evacuated and purged with argon as above and THF (3.0 mL) added via syringe. The mixture was stirred for 5 minutes to generate a colorless homogeneous solution which was cooled to −78° C. and added via canula to the zirconium solution. The mixture was stirred for 15 minutes at −78° C. to yield a bright yellow solution which was treated with 2-cyclohexenone (0.048 mL, 0.50 mmol). After 10 minutes the mixture was quenched with 10 mL of 10% NH$_4$OH in saturated NH$_4$Cl. The product was extracted with 3×30 mL of ether and dried over Na$_2$SO$_4$. The solution was then filtered through a pad of celite and the solvent removed in vacuo. The resulting residue was submitted to flash chromatography on silica gel (Petroleum Ether/Ethyl Acetate, 9/1) to give a 73% yield (0.076 g) of 3-(1-octen-1-yl)-cyclohexanone (product 2 in Table I) as a colorless oil which gave satisfactory IR, NMR, MS and HRMS data.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

TABLE I

| Educt | Acetylene | Conditions | Product | Yield(%)* |
|---|---|---|---|---|
| 1 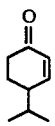 | ≡—⟩—O-Si(Ph)(Ph)⟨ | THF/DME −78°, 15 min | 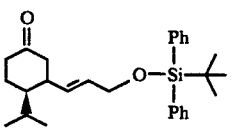 | quant |

TABLE I-continued

| Educt | Acetylene | Conditions | Product | Yield(%)* |
|---|---|---|---|---|
| 2  | ≡—n-C$_5$H$_{13}$ | THF/Et$_2$O<br>−78°, 5 min | 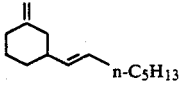 | 86 |
| 3  | ≡—⌬ | THF, BF$_3$<br>−78°, 1h |  | 71 |
| 4 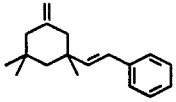 |  | THF/Et$_2$O<br>−78°, 10 min | 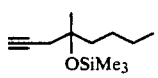 | 81 |
| 5 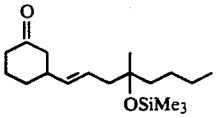 | ≡—n-C$_5$H$_{13}$ | THF/Et$_2$O<br>−60 to −50°, 1h | 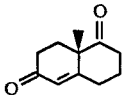 | 50(71)** |
| 6 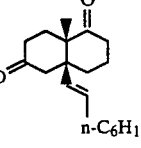 |  | *THF<br>−78°, 3.5h | 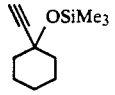 | 82 |
| 7 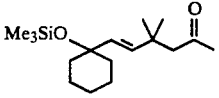 | 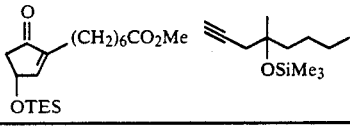 | THF/Et$_2$O<br>−78°, 10 min |  | 92 |

*Isolated, chromatographically pure materials; fully characterized by IR, NMR, Mass spectrometry (High and Low Resolution).
**Yield based on recovered starting material.

What is claimed is:

1. A method for preparing a cuprate complex of general formula I

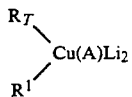

wherein R$_T$ is an anionic ligand for carbon-to-carbon bond formation;
R$^1$ is different from R$_T$ and is selected from the group consisting of alkyl, alkenyl, alkynyl, allylic, aryl, benzylic and heterocyclic moieties, —BR$^3$ wherein B is O or S and R$^3$ is an alkyl, alkenyl, alkynyl, allylic, aryl, benzylic or heterocyclic moiety, and —NR$^4$R$^5$ wherein R$^4$ and R$^5$ are the same or different and each is an alkyl, alkenyl, alkynyl, allylic, aryl, benzylic or heterocyclic moiety, said moieties being unsubstituted or substituted by non-interfering substituents; and A is CN or SCN, which comprises:

reacting a zirconium intermediate of general formula II

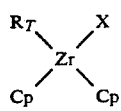

wherein Cp represents a cyclopentadienyl moiety which is unsubstituted or substituted by non-interfering substituents, X is halogen and R$_T$ is as previously defined, with one equivalent each of a compound of general formula R'Li, a compound of general formula R"Li, a compound of general formula R'" Li, and a compound of general formula Cu(A) or Cu(A).nLiX, wherein n is an integer from 1 to 10 and R', R" and R'" , may be the same or different and each is defined in the same manner as R$^1$, to provide the compound of general formula I, wherein R$^1$ corresponds to one of R', R" and R'".

2. A method according to claim 1, wherein R$_T$ is an anionic ligand selected from the group consisting of alkyl, alkenyl, aryl, allylic and benzylic ligands, said ligand being unsubstituted or substituted by non-interfering substituents.

3. A method according to claim 1, wherein R$_T$ is a beta side chain of a natural or synthetic prostaglandin, whrein the hydroxy groups are optionally protected.

4. A method according to claim 2, wherein said reacting is carried out below room temperature.

5. A method according to claim 4, wherein said reacting is carried out at about −78+ C.

6. A method for preparing a cuprate complex of general formula I

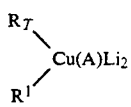

wherein $R_T$ is an anionic ligand for carbon-to-carbon bond formation;

$R^1$ is different from $R_T$ and is selected from the group consisting of alkyl, alkenyl, alkynyl, allylic, aryl, benzylic and heterocyclic moieties, $-BR^3$ wherein B is O or S and $R^3$ is an alkyl, alkenyl, alkynyl, allylic, aryl, benzylic or heterocyclic moiety, and $-NR^4R^5$ wherein $R^4$ and $R^5$ are the same or different and each is an alkyl, alkenyl, alkynyl, allylic, aryl, benzylic or heterocyclic moiety, said moieties being unsubstituted or substituted by non-interfering substituents; and A is CN or SCN, which comprises:

reacting a zirconium intermediate of general formula II

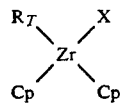

wherein Cp represents a cyclopentadienyl moiety which is unsubstituted or substituted by non-interfering substituents, X is halogen and $R_T$ is as previously defined, with one equivalent each of a compound of general formula R'Li, a compound of general formula R"Li and a compound of general formula R'" Cu(A)Li, wherein R', R" and R'" may be the same or different and each is defined in the same manner as $R^1$ to provide the compound of general formula I, wherein $R^1$ corresponds to one of R', R" and R'".

7. A method according to claim 6, wherein $R_T$ is an anionic ligand selected from the group consisting of alkyl, alkenyl, aryl, allylic and benzylic ligands, said ligand being unsubstituted or substituted by interfering substituents.

8. A method according to claim 6, wherein $R_T$ is a beta side chain of a natural or synthetic prostaglandin, wherein the hydroxy groups are optionally protected.

9. A method according to claim 6, wherein said reacting is carried out below room temperature.

10. A method according to claim 9, wherein said reacting is carried out at about $-78°$ C.

* * * * *

UNITED STATES PATENT AND TRADEMARK OFFICE
CERTIFICATE OF CORRECTION

PATENT NO. : 5,166,382
DATED : November 24, 1992
INVENTOR(S) : Lipshutz et al.

It is certified that error appears in the above-identified patent and that said Letters Patent is hereby corrected as shown below:

Title page, second line, replace "Howard et al." with --Lipshutz et al.--.

Col. 1, line 59, after "cuprates" insert --.-- (a period).
Col. 1, line 63, delete "Li2" and insert --Li$_2$.--.
Col. 2, line 13, after pathways insert --.-- (a period).
Col. 4, line 34, delete "R$_2$" and insert --R$^2$--.
Col. 6, Scheme 1, line A, line 2., delete "R$_2$'" and insert --R'$_2$--.
Col. 6, Scheme 2, delete "R$^8$" and insert --R$^B$--.
Col. 6, line 36, delete "-transfer" and insert --transfer--.
Col. 8, line 3, delete "15(6)." and insert --15(6),--.
Col. 8, line 6, after "vinylzirconate)" insert --;--.
Col. 8, line 61, after "-78° C.)" delete "." (a period).
Col. 9, line 65, delete "cboled" and insert --cooled--.
Col. 10, line 13, insert a hyphen after "4" and delete the hyphen after "isopropyl" to read --3-(1-t-butyldiphenyl-siloxy-2-propen-3-yl)-4-isopropylcyclohexanone--.
Col. 10, line 54, add a space between "products 3-6" and "of" to read --products 3-6 of--.
Col. 11, line 10, delete "1 0 mmol)." and insert --1.0 mmol).--.
Col. 11, line 31, delete entire line and insert
--3-(1-Phenylethen-2-yl)-3,5,5-trimethylcyclohexanone--.
Col. 11, line 55, delete "which." and insert --which--.

UNITED STATES PATENT AND TRADEMARK OFFICE
CERTIFICATE OF CORRECTION

| | | |
|---|---|---|
| PATENT NO. : | 5,166,382 | |
| DATED : | November 24, 1992 | |
| INVENTOR(S) : | Lipshutz et al. | |

It is certified that error appears in the above-identified patent and that said Letters Patent is hereby corrected as shown below:

Col. 12, line 16, delete entire line and insert
--Preparation of 3-(1-octen-1-yl)-cyclohexanone--.
Table I, line 6, in the column headed "Conditions", delete "*THF" and insert --THF--.
Col. 14, line 51, after "R'" ", delete the comma.
Col. 14, line 62, delete "whrein" and insert --wherein--.
Col. 14, line 66, delete "-78+ C." and insert -- -78° C.--.
Col. 16, line 21, delete "interfering" and insert --non-interfering--.

Signed and Sealed this

Eighteenth Day of January, 1994

*Attest:*

BRUCE LEHMAN

*Attesting Officer*    *Commissioner of Patents and Trademarks*